(12) United States Patent
Staby

(10) Patent No.: US 7,276,590 B1
(45) Date of Patent: Oct. 2, 2007

(54) ION EXCHANGE CHROMATOGRAPHY OF PROTEINS AND PEPTIDES

(75) Inventor: Arne Staby, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/671,461

(22) Filed: Sep. 27, 2000

Related U.S. Application Data

(62) Division of application No. 09/522,694, filed on Mar. 10, 2000, now Pat. No. 6,451,987.

(60) Provisional application No. 60/179,335, filed on Jan. 31, 2000, provisional application No. 60/125,882, filed on Mar. 24, 1999.

(30) Foreign Application Priority Data

| Mar. 15, 1999 | (DK) | ................................ 1999 00360 |
| Jan. 19, 2000 | (DK) | ................................ 2000 00083 |

(51) Int. Cl.
*C07K 1/00* (2006.01)

(52) U.S. Cl. ...................... 530/412; 530/350; 530/300; 530/416; 530/417; 435/7.1

(58) Field of Classification Search ................ 530/412, 530/350, 300, 416, 417; 435/7.1
See application file for complete search history.

(56) References Cited

U.S. PATENT DOCUMENTS

| 3,907,676 A | | 9/1975 | Jorgensen |
| 4,129,560 A | | 12/1978 | Zoltobrocki |
| 4,361,510 A | | 11/1982 | Mitra ......................... 260/112 |
| 5,101,013 A | | 3/1992 | Dorschug et al. |
| 5,344,918 A | | 9/1994 | Dazey et al. ................ 530/381 |
| 5,606,031 A | * | 2/1997 | Lile et al. .................... 530/416 |
| 6,113,911 A | * | 9/2000 | Binz et al. ............... 424/211.1 |
| 2003/0027996 A1 | | 2/2003 | Staby ......................... 530/416 |
| 2003/0103980 A1 | * | 6/2003 | Korc et al. .............. 424/155.1 |

FOREIGN PATENT DOCUMENTS

| EP | 0 207 727 | 1/1987 |
| EP | 0 699 686 A2 | 3/1996 |
| EP | 0 708 179 A2 | 4/1996 |
| EP | 0 849 277 | 6/1998 |
| WO | WO87/06941 | 11/1987 |
| WO | WO90/00176 | 1/1990 |
| WO | WO90/00177 | 1/1990 |
| WO | WO90/11296 | 10/1990 |
| WO | WO91/11457 | 8/1991 |
| WO | WO96/32414 | 10/1996 |
| WO | WO98/08871 | 3/1998 |
| WO | WO98/08872 | 3/1998 |

OTHER PUBLICATIONS

Johnson et al., Ion Exchange in "Basic Liquid Chromatography", pp. 116-148 (1978), Varian Associates, Inc.*
Dizdaroglu et al., Abstract, BIOSIS accession No. 198274065982.
Stadalius et al., Abstract, BIOSIS accession No. 198783093472.
Lamy et al., Archives of Biochemistry and Biophysics, vol. 193, No. 1, pp. 140-149 (Mar. 1979).
Brange et al., Acta Pharm. Nord., vol. 4, No. 4, pp. 223-232 (1992).
Bjoern et al., Activation of Coagulation Factor VII to VIIa, Res. Discl. No. 26960, pp. 564-565 (Sep. 1986).
Biomedical Research Foundation, Tokyo (1988), 9:47-51.
Schmidt et al., "Glucagon-like peptide-1 but not glucagons-like peptide-2 stimulates insulin release from isolated rat pancreatic islets" Diabetologia, vol. 28, pp. 704-707 (1985).
Kagaku et al., Activation of Coagulation of Factor VII to VIIa Research Disclosure; pp. 564-565 (Sep. 1986).
Abstract of Japanese Patent JP 10059866; "Preparation of blood coagulation factor VII and/or activated blood coagulation factor VII-by developing solution containing factor VII with anion exchange resin".
Abstract of Japanese Patent JP 10059867; "Activation of Blood coagulation Factor VII- by ion exchange purification of a solution containing Factor VII".
M. Raida et al. "Liquid Chromatography and Electrospray Mass Spectrometric Mapping of Peptides from Human Plasma Filtrate" Journ of American Society of Mass Spectrometry. vol. 10, pp. 45-54 (1999).
Huskins et al., "Halibut Muscle 3-Phosphoglycerate Kinase. Chemicaland Physcial Properties of the Enzyme and Its Substrate Complexes" Biochemistry, vol. 21, pp. 4180-4189 (1982).
Kreymann et al (1988) FEBS Letters, vol. 242: pp. 167-170.

* cited by examiner

*Primary Examiner*—Chih-Min Kam
(74) *Attorney, Agent, or Firm*—Richard W. Bork; Reza Green; Len S. Smith

(57) ABSTRACT

The present invention relates to an ion exchange chromatography process for purifying a peptide from a mixture containing the peptide and related impurities, and to an industrial method including such ion exchange chromatography process.

21 Claims, 8 Drawing Sheets

ION EXCHANGE CHROMATOGRAPHY OF PROTEINS AND PEPTIDES

CROSS-REFERENCE TO RELATED APPLICATIONS

This application is a divisional of Ser. No. 09/522,694 filed Mar. 10, 2000, now U.S. Pat. No. 6,451,987 and claims priority under 35 U.S.C. 119 of U.S. provisional application Nos. 60/125,882 and 60/179,335 filed Mar. 24, 1999 and Jan. 31, 2000, respectively, and of Danish application nos. 1999 00360 and 2000 00083 filed Mar. 15, 1999 and Jan. 19, 2000, respectively, the contents of which are fully incorporated herein by reference.

BACKGROUND OF THE INVENTION

1. Field of the Invention

The present invention relates to an ion exchange chromatography process for purifying a peptide from a mixture containing said peptide and related impurities and to an industrial including such ion exchange chromatography process.

2. Description of the Related Art

For the purification and analysis of proteins and peptides, chromatography is a well-known and widely used method. A number of different chromatographic principles are applied, among these ion exchange chromatography (IEC). The IEC principle includes two different approaches: anion exchange and cation exchange according to the charge of the ligands on the ion exchange resin. A conventional IEC purification process usually consists of one or more: equilibration sections, application or loading sections, wash sections, elution sections, and regeneration sections (cf. Remington's Pharmaceutical Sciences, Gennaro, ed., Mack Publishing Co., Easton, Pa., 1990, or Remington: The Science and Practice of Pharmacy, 19th Edition (1995)).

The main principle of elution in IEC in industrial purification processes is salt component gradients in an aqueous buffer solution at constant pH, either as step or linear gradients (cf. S. Bjørn and L. Thim, Activation of Coagulation Factor VII to VIIa, Res. Discl. No. 269, 564–565, 1986). Isocratic elution is possible, but seldom used. Organic solvents or modifiers have occasionally been added to the solutions to keep the protein or peptide on the desired form or just in solution (cf. K. H. Jørgensen, Process for Purifying Insulin, U.S. Pat. No. 3,907,676, Sep. 23, 1975; and J. Brange, O. Hallund and E. Sørensen, Chemical Stability of Insulin 5. Isolation, Characterisation and Identification of Insulin Transformation Products, Acta Pharm. Nord. 4(4), 223–232, 1992). Also, the change in pH may occasionally be employed to elute the target protein (cf. J. Lamy, J. Lamy, J. Weill, Arch. Biochem. Biophys. 193, 140–149, 1979).

BRIEF SUMMARY OF THE INVENTION

In contrast to the above described IEC techniques for purification of any protein or peptide, consisting of one or more equilibration steps, application or loading steps, wash steps, elution steps, and regeneration steps, the present invention relates to a novel elution technique which is the combination of elution in a solution comprising an organic modifier with the subsequent elution in an aqueous solution at the same or a different pH optionally followed by a regeneration step. The equilibration solution and the sample for application may or may not contain the organic modifier. The elution of the peptide occurs at non-denaturing conditions (in a solution free of organic modifier). Moreover, the elution of the peptide is performed in a single peak.

Accordingly, in a broad aspect the present invention relates to a cation exchange chromatography process for purifying a peptide from a mixture comprising said peptide and related impurities, comprising the steps of:

a) eluting said related impurities of said mixture in a solution comprising an organic modifier, water, optionally a salt component and optionally a buffer, at a linear or step gradient or isocratically in salt component, and at pH-values optionally maintained with a buffer so that said peptide has a positive local or overall net charge and said related impurities have a local or overall positive net charge which is lower than the positive net charge of said peptide so as to remove said related impurities, b) subsequently, eluting said peptide by a step or linear change to an aqueous solvent optionally with a salt component, at the same or higher pH-values optionally maintained with a buffer.

In another broad aspect the present invention relates to a cation exchange chromatography process for purifying a peptide from a mixture comprising said peptide and related impurities, comprising the steps of:

a) eluting said related impurities of said mixture in a solution consisting essentially of an organic modifier, water, optionally a salt component and optionally a buffer, at a linear or step gradient or isocratically in salt component, and at pH-values optionally maintained with a buffer so that said peptide has a positive local or overall net charge and said related impurities have a local or overall positive net charge which is lower than the positive net charge of said peptide so as to remove said related impurities, b) subsequently, eluting said peptide by a step or linear change to an aqueous solvent optionally with a salt component, at the same or higher pH-values optionally maintained with a buffer.

In another broad aspect the present invention relates to an anion exchange chromatography process for purifying a peptide from a mixture comprising said peptide and related impurities, comprising the steps of:

a) eluting said related impurities of said mixture in a solution comprising an organic modifier, water, optionally a salt component and optionally a buffer, at a linear or step gradient or isocratically in salt component, and at pH-values optionally maintained with a buffer so that said peptide has a negative local or overall net charge and said related impurities have a local or overall negative net charge which is lower than the negative net charge of said peptide so as to remove said related impurities, b) subsequently, eluting said peptide by a step or linear change to an aqueous solvent optionally with a salt component, at the same or lower pH-values optionally maintained with a buffer.

In another broad aspect the present invention relates to an anion exchange chromatography process for purifying a peptide from a mixture comprising said peptide and related impurities, comprising the steps of:

a) eluting said related impurities of said mixture in a solution consisting essentially of an organic modifier, water, optionally a salt component and optionally a buffer, at a linear or step gradient or isocratically in salt component, and at pH-values optionally maintained with a buffer so that said peptide has a negative local or overall net charge and said related impurities have a local or overall negative net charge which is lower than the negative net charge of said peptide so as to remove said related impurities, b) subsequently, eluting said peptide by a step or linear change to an aqueous solvent optionally with a salt component, at the same or lower pH-values optionally maintained with a buffer.

In the above aspects of the present process the elution in step a) could also be considered a washing step of related impurities.

The elution of the peptide in step b) occurs at nondenaturing conditions (in a solution free of organic modifier). Thus, the peptide is eluted to an aqueous solution with a solution comprising water and optionally a salt component, an acid or base, and/or a buffer, but without the presence of an organic modifier.

In one embodiment of the present invention the ratio of organic modifier to water, on a weight percent basis, is from 1:99 to 99:1, such as from 1:99 to 80:20, 20:80 to 80:20, 30:70 to 70:30, 35:50 to 50:35, or 40:50 to 50:40. Each of these ranges constitutes an alternative embodiment of the present invention.

In further embodiments of the present invention the organic modifier is selected from $C_{1-6}$-alkanol, $C_{1-6}$-alkenol or $C_{1-6}$-alkynol, urea, guanidine, or $C_{1-6}$-alkanoic acid, such as acetic acid, $C_{2-6}$-glycol, $C_{3-7}$-polyalcohol including sugars, preferably $C_{1-6}$-alkanol and $C_{2-6}$-glycol, more preferably methanol, ethanol, propanols and butanols and hexyl glycols, most preferably ethanol and 2-propanol. Each of these organic modifiers constitutes an alternative embodiment of the present invention.

In a further embodiment of the present invention the salt component in step a) is selected from any organic or inorganic salt and mixtures thereof, preferably NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof, most preferred sodium acetate, potassium acetate, ammonium acetate, NaCl, $NH_4Cl$, KCl. Each of these salt components constitutes an alternative embodiment of the present invention.

In a further embodiment of the present invention the gradient in salt component in step a) is a step gradient in the salt component.

In a further embodiment of the present invention the salt component in step a) is present in a step concentration selected from the range of 0.1 mmol/kg to 3000 mmol/kg, preferably 1 mmol/kg to 1000 mmol/kg, more preferably 5 mmol/kg to 500, most preferably 20 mmol/kg to 300 mmol/kg. Each of these ranges constitutes an alternative embodiment of the present invention.

In a further embodiment of the present invention the salt component gradient in step a) is a linear gradient in salt component.

In a further embodiment of the present invention the salt component in step a) is present in a linear concentration selected from 0.1 mmol/kg to 3000 mmol/kg, preferably 1 mmol/kg to 1000 mmol/kg, more preferably 5 mmol/kg to 500, most preferably 20 mmol/kg to 300 mmol/kg. Each of these linear concentrations constitutes an alternative embodiment of the present invention.

In a further embodiment of the present invention no salt component is present in step a.

In a further embodiment of the present invention the salt component in step b) is selected from any organic or inorganic salt, preferably NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof, most preferred sodium acetate, potassium acetate, ammonium acetate, NaCl, $NH_4Cl$, KCl. Each of these salt components constitutes an alternative embodiment of the present invention.

In a further embodiment of the present invention the salt component in step b) is present in a concentration selected from the range of 0.1 mmol/kg to 3000 mmol/kg, preferably 1 mmol/kg to 1000 mmol/kg, more preferably 5 mmol/kg to 500, most preferably 20 mmol/kg to 300 mmol/kg. Each of these ranges constitutes an alternative embodiment of the present invention.

In a further embodiment of the present invention no salt component is present in step b).

In a further embodiment of the present invention the buffer in step a) or b) is independently selected from citrate buffers, phosphate buffers, tris buffers, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, tri-ethanol amine, imidazole buffers, pyridine buffers and barbiturate buffers and mixtures thereof, preferably citric acid, sodium citrate, sodium phosphate, phosphoric acid, glutamic acid, sodium glutamate, glycin, sodium carbonate, potassium citrate, potassium phosphate, potassium glutamate, potassium carbonate, tris-hydroxymethyl amino methane and boric acid and mixtures thereof. Each of these buffers constitutes an alternative embodiment of the present invention.

In a further embodiment of the present invention the buffer in step a) is present in a concentration selected from the range of 0.1 mmol/kg to 500 mmol/kg, preferably 1 mmol/kg to 200 mmol/kg, more preferably 5 mmol/kg to 100 mmol/kg, most preferably 10 mmol/kg to 50 mmol/kg. Each of these ranges constitutes an alternative embodiment of the present invention.

In a further embodiment of the present invention the buffer in step b) is present in a concentration selected from the range of 0.1 mmol/kg to 1000 mmol/kg, preferably 1 mmol/kg to 400 mmol/kg, most preferably 50 mmol/kg to 200 mmol/kg. Each of these ranges constitutes an alternative embodiment of the present invention.

In a further embodiment of the present invention no buffer is present in step a).

In a further embodiment of the present invention no buffer is present in step b).

In a further embodiment of the present invention the peptide to be purified is selected from polypeptides, oligopeptides; proteins, receptors, vira, as well as homologues, analogues and derivatives thereof, preferably glucagon, hGH, insulin, aprotinin, FactorVII, TPA, FactorVIIa, FFR-FactorVIIa, heparinase, ACTH, Heparin Binding Protein, corticotropin-releasing factor, angiotensin, calcitonin, insulin, glucagon-like peptide-1, glucagon-like peptide-2, insulin-like growth factor-1, insulin-like growth factor-2, fibroblast growth factors, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods, DPP IV, interleukins, immunoglobulins, complement inhibitors, serpin protease inhibitors, cytokines, cytokine receptors, PDGF, tumor necrosis factors, tumor necrosis factors receptors, growth factors and analogues as well as derivatives thereof, more preferably glucagon, hGH, insulin, aprotinin, Factor-VII, FactorVIIa, FFR-FactorVIIa, heparinase, glucagon-like peptide-1, glucagon-like peptide-2 and analogues as well as derivatives thereof, such as Val$^8$GLP-1 (7-37), Thr$^8$GLP-1 (7-37), Met$^8$GLP-1(7-37), Gly$^8$GLP-1(7-37), Val$^8$GLP-1(7-36) amide, Thr$^8$GLP-1(7-36) amide, Met$^8$GLP-1(7-36) amide, Gly$^8$GLP-1(7-36) amide, Arg$^{34}$GLP-1(7-37), human insulin, and B28IsoAsp insulin. Each of these peptides constitutes an alternative embodiment of the present invention.

Figure 1:
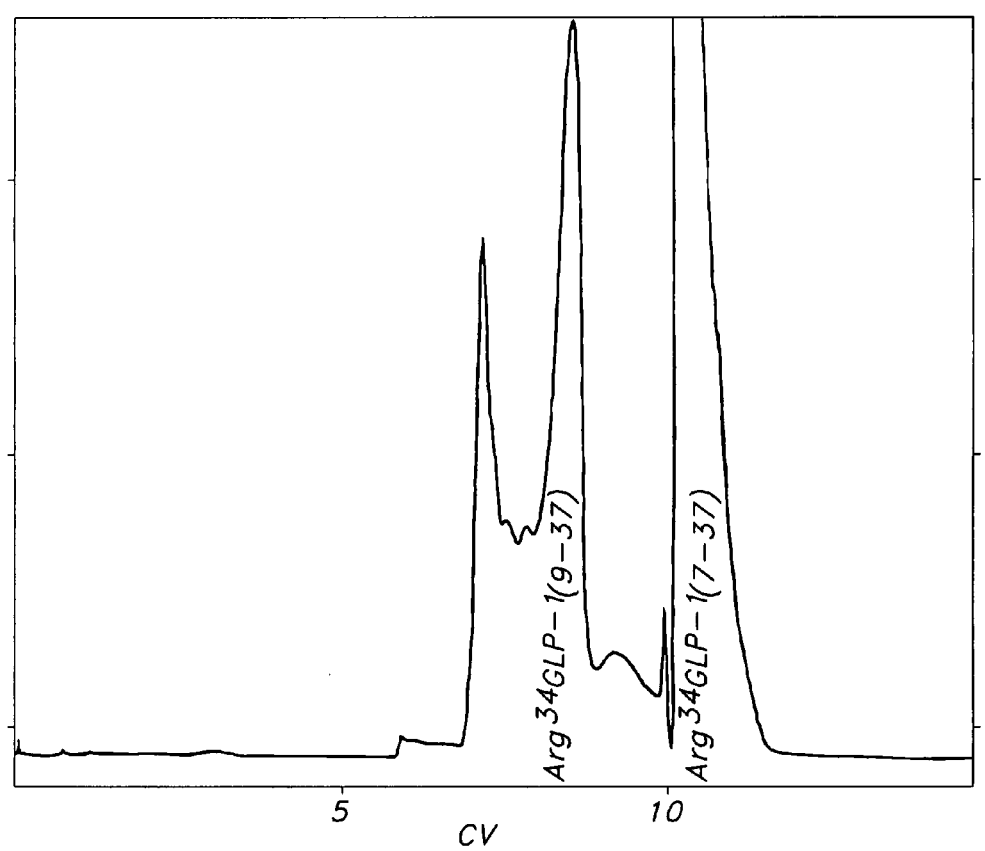
FIG. 1 is a chromatograph obtained as described in Example 1.

As an example illustrating the present invention, histidine has a predominant positive net charge below pH~6.5, thus for cation exchange the wash or elution section with organic solvent or modifier could be performed below pH 6.5 to remove a truncated form missing histidine, and subsequent elution of the target protein or peptide in the aqueous solvent could be performed above pH 6.5. As a second example, the carboxyl group of the C-terminal amino acid has a predominant negative net charge above pH~3.1, thus for anion exchange the wash or elution section with organic solvent could be performed above pH 3.1 to remove a form extended to an amide, and subsequent elution of the target protein or peptide in the aqueous solvent could be performed both above or below pH 3.1. As a third example, aspartic acid has a predominant negative net charge above pH~4.4, thus for anion exchange the wash or elution section with organic solvent could be performed above pH 4.4 to remove a truncated form missing aspartic acid, and subsequent elution of the target protein or peptide in the aqueous solvent could be performed below pH 4.4. As a fourth example, glutamic acid has a predominant negative net charge above pH~4.4, thus for anion exchange the wash or elution section with organic solvent could be performed above pH 4.4 to remove a truncated form missing glutamic acid, and subsequent elution of the target protein or peptide in the aqueous solvent could be performed below pH 4.4. As a fifth example, γ-carboxy glutamic acid has a predominant negative net charge above pH~4.4, thus for anion exchange the wash or elution section with organic solvent could be performed above pH 4.4 to remove a form missing one or more γ-carboxy groups of specific glutamic acid residues, and subsequent elution of the target protein or peptide in the aqueous solvent could be performed below pH 4.4. As a sixth example, the amino group of the N-terminal amino acid has a predominant positive net charge below pH~8.0, thus for cation exchange the wash or elution section with organic solvent could be performed below pH 8.0 to remove a form extended with an acyl group, and subsequent elution of the target protein or peptide in the aqueous solvent could be performed both above or below pH 8.0. As a seventh example, cysteine has a predominant negative net charge above pH~8.5, thus for anion exchange the wash or elution section with organic solvent could be performed above pH 8.5 to remove a poorly folded form resulting in free cysteine residues, and subsequent elution of the target protein or peptide in the aqueous solvent could be performed below pH 8.5. As an eighth example, tyrosine has a predominant negative net charge above pH~10.0, thus for anion exchange the wash or elution section with organic solvent could be performed above pH 10.0 to remove a truncated form missing a tyrosine residue, and subsequent elution of the target protein or peptide in the aqueous solvent could be performed below pH 10.0. As a ninth example, lysine has a predominant positive net charge below pH~10.0, thus for cation exchange the wash or elution section with organic solvent could be performed below pH 10.0 to remove a form acylated in the side chain of the lysine residue, and subsequent elution of the target protein or peptide in the aqueous solvent could be performed above or below pH 10.0. As a tenth example, arginine has a predominant positive net charge below pH~12.0, thus for anion exchange the wash or elution section with organic solvent could be performed below pH 12.0 to remove a truncated form missing an arginine residue, and subsequent elution of the target protein or peptide in the aqueous solvent could be performed above pH 12.0. (p$K_A$-values used in these examples are from: L. Stryer. Biochemistry, 3$^{rd}$ edition, W. H. Freeman and Company, New York, Table 2-1 page 21).

Specific peptide examples of the above-mentioned method are separation of Arg$^{34}$GLP-1(7-37) and Arg$^{34}$GLP-1(9-37) by cation exchange chromatography, human insulin and B30 human insulin ethyl ester by anion exchange chromatography, B28IsoAsp insulin and DesB23-30 insulin by anion exchange chromatography, prothrombin and des-γ-carboxy-Glu prothrombin by anion exchange chromatography, Arg$^{34}$GLP-1 (7-37) and Arg$^{34}$GLP-1(10-37) by anion exchange chromatography, Lys$^{B29}$-(N-ε(α-tetradecanoyl))-desB30 insulin and DesB30 insulin by cation exchange chromatography, Lys$^{B29}$-(N-ε(α-tetradecanoyl))-desB30 insulin and Lys$^{B29}$-(N-ε(α-tetradecanoyl))-A1-(N-ε(α-tetradecanoyl))-desB30 insulin by cation exchange chromatography, aprotinin and Des-Arg-Pro-aprotinin by cation exchange chromatography, and Glucagon$_{(1-29)}$ and Glucagon$_{(6-29)}$ by anion exchange chromatography.

The peptides can be produced by a method which comprises culturing or fermenting a host cell containing a DNA sequence encoding the polypeptide and capable of expressing the polypeptide in a suitable nutrient medium under conditions permitting the expression of the peptide, after which the resulting peptide is recovered from the culture or fermentation broth. Hereinafter, culturing will be used to cover both culturing and fermenting and the like.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including, optionally lysis of cells, separating the host cells from the medium by centrifugation or filtration, precipitating the proteinaceous components of the supernatant or filtrate by means of a salt, e.g. ammonium sulphate, purification by conventional purification techniques, such as chromatographic techniques, if necessary, purification by ion exchange chromatography according to the present invention, and subsequently, subjecting to analytical tests, e.g. PAGE, IEF, if necessary, subjecting to further purification, if necessary, and isolation of the pure peptide.

During the recovery of the resulting peptide from the culture medium, but before purification by ion exchange chromatography according to the present invention, the mixture comprising the peptide and related impurities may optionally be chemically modified by conventional techniques, e.g. by alkylation, acylation, ester formation or amide formation or the like.

The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the peptide may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. The DNA sequence may also be prepared by polymerase chain reaction using specific primers, for instance as described in U.S. Pat. No. 4,683,202 or Saiki et al., *Science* 239 (1988), 487–491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a peptide into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, vira, e.g. baculo virus; yeast, fungi, insect cells and higher eukaryotic cells. Examples of suitable host cells well known and used in the art are, without limitation, *E. coli, Saccharomyces cerevisiae*, or mammalian BHK or CHO cell lines.

Some of the peptides, in particular the oligopeptides, can be produced according to conventional organic peptide synthetic chemistry. The resulting synthetic mixture may then be chemically modified, e.g. by alkylation, acylation, ester formation or amide formation or the like, and purified, or purified as it is and then modified chemically as mentioned above.

Preparation of Factor VIIa

Human purified factor VIIa suitable for use in the present invention is preferably made by DNA recombinant technology, e.g. as described by Hagen et al., *Proc. Natl. Acad. Sci. USA* 83: 2412–2416, 1986 or as described in European Patent No. 200.421 (ZymoGenetics). Factor VIIa produced by recombinant technology may be authentic factor VIIa or a more or less modified factor VIIa provided that such factor VIIa has substantially the same biological activity for blood coagulation as authentic factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

Factor VII may also be produced by the methods described by Broze and Majerus, *J. Biol. Chem.* 255 (4): 1242–1247, 1980 and Hedner and Kisiel, *J. Clin. Invest.* 71: 1836–1841, 1983. These methods yield factor VII without detectable amounts of other blood coagulation factors. An even further purified factor VII preparation may be obtained by including an additional gel filtration as the final purification step. Factor VII is then converted into activated FVIIa by known means, e.g. by several different plasma proteins, such as factor XIIa, IX a or Xa. Alternatively, as described by Bjoern et al. (Research Disclosure, 269 September 1986, pp. 564–565), factor VII may be activated by passing it through an ion-exchange chromatography column, such as Mono Q® (Pharmacia fine Chemicals) or the like.

Modified or Inactivated FVIIa (FVIIai) May be Produced by the Following Methods:

International Application No. WO 92/15686 relates to modified Factor VIIa, polynucleic acid and mammalian cell lines for the production of modified Factor VIIa, and compositions comprising modified Factor VIIa for inhibiting blood coagulation.

Modified Factor VII may be encoded by a polynucleotide molecule comprising two operatively linked sequence coding regions encoding, respectively, a pre-pro peptide and a gla domain of a vitamin K-dependent plasma protein, and a gla domain-less Factor VII protein, wherein upon expression said polynucleotide encodes a modified Factor VII molecule which does not significantly activate plasma Factors X or IX, and is capable of binding tissue factor.

The catalytic activity of Factor VIIa can be inhibited by chemical derivatization of the catalytic centre, or triad. Derivatization may be accomplished by reacting Factor VII with an irreversible inhibitor such as an organophosphor compound, a sulfonyl fluoride, a peptide halomethyl ketone or an azapeptide, or by acylation, for example. Preferred peptide halomethyl ketones include PPACK (D-Phe-Pro-Arg chloromethyl-ketone; (see U.S. Pat. No. 4,318,904, incorporated herein by reference), D-Phe-Phe-Arg and Phe-Phe-Arg chloromethylketone (FFR-cmk); and DEGRck (dansyl-Glu-Gly-Arg chloromethylketone).

The catalytic activity of Factor VIIa can also be inhibited by substituting, inserting or deleting amino acids. In preferred embodiments amino acid substitutions are made in the amino acid sequence of the Factor VII catalytic triad, defined herein as the regions, which contain the amino acids, which contribute to the Factor VIIa catalytic site. The substitutions, insertions or deletions in the catalytic triad are generally at or adjacent to the amino acids which form the catalytic site. In the human and bovine Factor VII proteins, the amino acids, which form a catalytic "triad", are $Ser_{344}$, $Asp_{242}$, and $His_{193}$ (subscript numbering indicating position in the sequence). The catalytic sites in Factor VII from other mammalian species may be determined using presently available techniques including, among others, protein isolation and amino acid sequence analysis. Catalytic sites may also be determined by aligning a sequence with the sequence of other serine proteases, particularly chymotrypsin, whose active site has been previously determined (Sigler et al., *J. Mol. Biol.*, 35:143–164 (1968), incorporated herein by reference), and there from determining from said alignment the analogous active site residues.

In preferred embodiments of human and bovine Factor VII, the active site residue $Ser_{344}$ is modified, replaced with Gly, Met, Thr, or more preferably, Ala. Such substitution could be made separately or in combination with substitution(s) at other sites in the catalytic triad, which includes $His_{193}$ and $Asp_{242}$.

The amino acids, which form the catalytic site in Factor VII, such as $Ser_{344}$, $Asp_{242}$, and $His_{193}$ in human and bovine Factor VII, may either be substituted or deleted. Within the present invention, it is preferred to change only a single amino acid, thus minimizing the likelihood of increasing the antigenicity of the molecule or inhibiting its ability to bind tissue factor, however two or more amino acid changes (substitutions, additions or deletions) may be made and combinations of substitution(s), addition(s) and deletion(s) may also be made. In a preferred embodiment for human and bovine Factor VII, $Ser_{344}$ is preferably substituted with Ala, but Gly, Met, Thr or other amino acids can be substituted. It is preferred to replace Asp with Glu and to replace His with Lys or Arg. In general, substitutions are chosen to disrupt the tertiary protein structure as little as possible. The model of Dayhoff et al. (in *Atlas of Protein Structure* 1978, Nat'l Biomed. Res. Found., Washington, D.C.), incorporated herein by reference, may be used as a guide in selecting other amino acid substitutions. One may introduce residue alterations as described above in the catalytic site of appropriate Factor VII sequence of human, bovine or other species and test the resulting protein for a desired level of inhibition of catalytic activity and resulting anticoagulant activity as described herein. For the modified Factor VII the catalytic activity will be substantially inhibited, generally less than about 5% of the catalytic activity of wild-type Factor VII of the corresponding species, more preferably less than about 1%.

The modified Factor VII may be produced through the use of recombinant DNA techniques.

The amino acid sequence alterations may be accomplished by a variety of techniques. Modification of the DNA sequence may be by site-specific mutagenesis. Techniques for site-specific mutagenesis are well known in the art and are described by, for example, Zoller and Smith (*DNA* 3:479–488, 1984). Thus, using the nucleotide and amino acid sequences of Factor VII, one may introduce the alteration(s) of choice. The modified FVIIa may also be produced by chemical methods.

FFR-FVIIa (that is, D-Phe-Phe-Arg-FVIIa)

EXAMPLE FFR Chloromethyl Ketone

Blockage of the Active Site of FVIIa with FFR Chloromethyl Ketone.

Blockage of the active site serine and histidine with chloromethyl ketone is a well-known method for irreversible inactivation of serine proteases. In order to optimise the blockage of a given protease it is important to choose a chloromethyl ketone derivative, which reacts specifically with the active site and with a fast on-rate. Such derivatives can be developed by attachment to the chloromethyl ketone group of an oligopeptide, which interacts, with the substrate-binding pocket of the particular serine protease of interest.

Glutamyl-Glycyl-Arginine chloromethyl ketone (EGR-ck or its Dansyl derivative, DEGR-ck) (S. Higashi, H. Nishimura, S. Fujii, K. Takada, S. Iwanaga, (1992) J. Biol. Chem. 267, 17990) or Prolyl-Phenyl-Arginine chloromethyl ketone (PFR-ck) (J. H. Lawson, S. Butenas, K. Mann, (1992) J. Biol. Chem. 267, 4834; J. Contrino, G. A. Hair, M. A. Schmeizl, F. R. Rickles, D. L. Kreutzer (1994) Am. J. Pathol. 145, 1315) have been applied as active site inhibitors of FVIIa. Compared with these chloromethyl ketones application of FFRck represents a rate increase of 10–70 fold.

The specificity of the reaction with FFR-chloromethyl ketone derivative of FVIIa was checked by HPLC and peptide mapping which showed that FVIIa had reacted with FFR-chloromethyl ketone in a 1:1 ratio such that >98% could be recovered as the expected product derivatized at histidine 193.

Inactivation of FVIIa by Various Chloromethyl Ketones:

3 μM FVIIa was incubated with 12 μM of chloromethyl ketone derivative in 50 mM Tris HCl, 100 mM NaCl, 5 mM $CaCl_2$, 0.01% Tween-80, pH 7.4. Samples were withdrawn at various time intervals as indicated and and diluted 20 times for activity measurements in 50 mM Tris HCl, 100 mM NaCl, 5 mM $CaCl_2$, 0.01% Tween-80, pH 7.4 containing 1 mM Ile-Pro-Arg-pNA. The residual FVIIa activity was measured by the increase in absorbance at 405 nm.

Usually, the mixture comprising the peptide and related impurities to be purified by ion exchange chromatography according to the present invention, will also contain amino acids, small peptides, large peptides, unrelated proteins, reactants, cell debris, HCP, endotoxins, and/or vira depending on whether recombinant DNA techniques and/or chemical modification techniques have been used or whether organic peptide synthetic chemistry techniques have been used.

Thus, any method, such as an industrial method, for producing a pure peptide, which includes an IEC process according to the present invention is also an aspect of the present application.

Accordingly, the present invention relates in a further aspect to an industrial method for producing a pure peptide, the method including a cation exchange chromatography process for purifying a peptide from a mixture comprising said peptide and related impurities, comprising the steps of:

a) eluting said related impurities of said mixture in a solution consisting essentially of an organic modifier, water, optionally a salt component and optionally a buffer, at a linear or step gradient or isocratically in salt component, and at pH-values optionally maintained with a buffer so that said peptide has a positive local or overall net charge and said related impurities have a local or overall positive net charge which is lower than the positive net charge of said peptide so as to remove said related impurities, b) subsequently, eluting said peptide by a step or linear change to an aqueous solvent optionally with a salt component, at the same or higher pH-values optionally maintained with a buffer.

The present invention relates in a further aspect to a method for isolating a peptide, the method including purification of a peptide from a mixture comprising said peptide and related impurities via a cation exchange chromatography process, the cation exchange chromatography process comprising the steps of:

a) eluting said related impurities of said mixture in a solution comprising an organic modifier, water, optionally a salt component and optionally a buffer, at a linear or step gradient or isocratically in salt component, and at pH-values optionally maintained with a buffer so that said peptide has a positive local or overall net charge and said related impurities have a local or overall positive net charge which is lower than the positive net charge of said peptide so as to remove said related impurities,
   b) subsequently, eluting said peptide by a step or linear change to an aqueous solvent optionally with a salt component, at the same or higher pH-values optionally maintained with a buffer;

and subsequently, if necessary, subjecting to analytical tests and/or further purification, and isolating said peptide in a conventional manner.

The present invention relates in a further aspect to a method for isolating a peptide, the method including purification of a peptide from a mixture comprising said peptide and related impurities via a cation exchange chromatography process, the cation exchange chromatography process comprising the steps of:

a) eluting said related impurities of said mixture in a solution consisting essentially of an organic modifier, water, optionally a salt component and optionally a buffer, at a linear or step gradient or isocratically in salt component, and at pH-values optionally maintained with a buffer so that said peptide has a positive local or overall net charge and said related impurities have a local or overall positive net charge which is lower than the positive net charge of said peptide so as to remove said related impurities,
   b) subsequently, eluting said peptide by a step or linear change to an aqueous solvent optionally with a salt component, at the same or higher pH-values optionally maintained with a buffer;

and subsequently, if necessary, subjecting to analytical tests and/or further purification, and isolating said peptide in a conventional manner.

The present invention relates in a further aspect to an industrial method for producing a pure peptide, the method including an anion exchange chromatography process for purifying a peptide from a mixture comprising said peptide and related impurities, comprising the steps of:

a) eluting said related impurities of said mixture in a solution consisting essentially of an organic modifier, water, optionally a salt component and optionally a buffer, at a linear or step gradient or isocratically in salt component, and at pH-values optionally maintained with a buffer so that said peptide has a negative local or overall net charge and said related impurities have a local or overall negative net charge which is lower than the negative net charge of said peptide so as to remove said related impurities, b) subsequently, eluting said peptide by a step or linear change to an aqueous solvent optionally with a salt component, at the same or lower pH-values optionally maintained with a buffer.

The present invention relates in a still further aspect to a method for isolating a peptide, the method including purification of a peptide from a mixture comprising said peptide and related impurities via an anion exchange chromatography process, the anion exchange chromatography process comprising the steps of:

a) eluting said related impurities of said mixture in a solution comprising an organic modifier, water, optionally a salt component and optionally a buffer, at a linear or step gradient or isocratically in salt component, and at pH-values optionally maintained with a buffer so that said peptide has a negative local or overall net charge and said related impurities have a local or overall negative net charge which is lower than the negative net charge of said peptide so as to remove said related impurities,
   b) subsequently, eluting said peptide by a step or linear change to an aqueous solvent optionally with a salt component, at the same or lower pH-values optionally maintained with a buffer;

and subsequently, if necessary, subjecting to analytical tests and/or further purification, and isolating said peptide in a conventional manner.

The present invention relates in a still further aspect to a method for isolating a peptide, the method including purification of a peptide from a mixture comprising said peptide and related impurities via an anion exchange chromatography process, the anion exchange chromatography process comprising the steps of:

a) eluting said related impurities of said mixture in a solution consisting essentially of an organic modifier, water, optionally a salt component and optionally a buffer, at a linear or step gradient or isocratically in salt component, and at pH-values optionally maintained with a buffer so that said peptide has a negative local or overall net charge and said related impurities have a local or overall negative net charge which is lower than the negative net charge of said peptide so as to remove said related impurities, b) subsequently, eluting said peptide by a step or linear change to an aqueous solvent optionally with a salt component, at the same or lower pH-values optionally maintained with a buffer;

and subsequently, if necessary, subjecting to analytical tests and/or further purification, and isolating said peptide in a conventional manner.

Any possible combination of two or more of the embodiments described herein, is comprised within the scope of the present invention.

The term "an organic modifier", as used herein, is intended to include an organic solvent or organic compound soluble in water or mixtures thereof, which modifier induces a favorable and changed selectivity between the unwanted related impurity or impurities and the peptide and the ion exchanger. Whether or not a selected modifier induces said selectivity will usually depend on the related impurity or impurities, and may be tested by trial-and-error. The organic modifier includes but is not limited to $C_{1-6}$-alkanol, $C_{1-6}$-alkenol or $C_{1-6}$-alkynol, urea, guanidine•HCl, or $C_{1-6}$-alkanoic acid, such as acetic acid, $C_{2-6}$-glycol, $C_{3-7}$-polyalcohol including sugars or mixtures thereof.

The term "$C_{1-6}$-alkanol", "$C_{1-6}$-alkenol" or "$C_{1-6}$-alkynol", as used herein, alone or in combination is intended to include those $C_{1-6}$alkane, $C_{1-6}$alkene or $C_{1-6}$alkyne groups of the designated length in either a linear or branched or cyclic configuration whereto is linked a hydroxyl (—OH) (cf. Morrison & Boyd, Organic Chemistry, $4^{th}$ ed). Examples of linear alcohols are methanol, ethanol, n-propanol, allyl alcohol, n-butanol, n-pentanol and n-hexanol. Examples of branched alcohols are 2-propanol and tert-butyl alcohol. Examples of cyclic alcohols are cyclo propyl alcohol and 2-cyclohexen-1-ol.

The term "$C_{1-6}$-alkanoic acid", as used herein, is intended to include a group of the formula R'COOH wherein R' is H or $C_{1-5}$alkyl, such as acetic, propionic, butyric, ?-methylbutyric, or valeric acid (cf. Morrison & Boyd, Organic Chemistry, $4^{th}$ ed).

The term "$C_{1-5}$-alkyl", as used herein, is intended to include a branched or straight alkyl group having from one to five carbon atoms. Typical $C_{1-5}$-alkyl groups include, but are not limited to, methyl, ethyl, n-propyl, iso-propyl, butyl, iso-butyl, sec-butyl, tert-butyl, pentyl, isopentyl, and the like (cf. Morrison & Boyd, Organic Chemistry, $4^{th}$ ed).

The term "$C_{2-6}$-glycol", as used herein, is intended to include a $C_{2-6}$-alkane containing two hydroxyl groups on different carbon atoms which may be adjacent or not. A typical $C_{2-6}$-glycol include, but is not limited to 1,2-ethanediol, 1,2-propanediol, or 2-methyl-2,4-pentanediol (cf. Morrison & Boyd, Organic Chemistry, $4^{th}$ ed).

The term "$C_{2-6}$-alkane", as used herein, is intended to include a branched or straight alkane group having from two to six carbon atoms. Typical $C_{2-6}$-alkane groups include, but are not limited to ethane, propane, iso-propane, butane, iso-butane, pentane, hexane and the like (cf. Morrison & Boyd, Organic Chemistry, $4^{th}$ ed).

The term "$C_{3-7}$-polyalcohol including sugars", as used herein, is intended to include a group of the formula $HOCH_2(CHOH)_nCH_2OH$ wherein n is an integer from 1–5, and monosaccharides such as mannose, glucose (cf. Morrison & Boyd, Organic Chemistry, $4^{th}$ ed).

The term "peptide" or "peptides", as used herein, is intended to include such polypeptides, oligopeptides, proteins, as well as homologues, analogues and derivatives thereof, which are capable of being produced by conventional recombinant DNA techniques as well as conventional synthetic methods. Such peptides include but are not limited to glucagon, hGH, insulin, aprotinin, FactorVII, TPA, FactorVIIa (NovoSeven®), available from Novo Nordisk A/S, Bagsvaerd, Denmark), FactorVIIai, FFR-FactorVIIa, heparinase, ACTH, corticotropin-releasing factor, angiotensin, calcitonin, insulin, glucagon-like peptide-1, glucagon-like peptide-2, insulin-like growth factor-1, insulin-like growth factor-2, gastric inhibitory peptide, growth hormone-releasing factor, pituitary adenylate cyclase activating peptides, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods, GIP, exendins, peptide histidine-methionine amide, helospectins, helodermin, pituitary adenylate cyclase activating peptide-related peptide, vasoactive intestinal polypeptide and analogues thereof, wherein analogues is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both. Derivatives are used in the present text to designate a peptide in which one or more of the amino acid residues of the parent peptide have been chemically modified, e.g. by alkylation, acylation, ester formation or amide formation or the like.

The term "salt component" as used herein, is intended to include any organic or inorganic salt, including but not limited to NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof (cf. Remington's Pharmaceutical Sciences, Gennaro, ed., Mack Publishing Co., Easton, Pa., 1990, or Remington: The Science and Practice of Pharmacy, 19th Edition (1995), or handbooks from Amersham-Pharmacia Biotech).

The term "a buffer" as used herein, is intended to include any buffer including but not limited to: citrate buffers, phosphate buffers, tris buffers, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, tri-ethanol amine, imidazole buffers, pyridine buffers and barbiturate buffers and mixtures thereof (cf. Remington's Pharmaceutical Sciences, Gennaro, ed., Mack Publishing Co., Easton, Pa., 1990, or Remington: The Science and Practice of Pharmacy, 19th Edition (1995), or handbooks from Amersham-Pharmacia Biotech).

The choice of starting pH, buffer and ionic strength is done according to well-known techniques such as conventional test-tube methods, cf. e.g. handbooks from Amersham-Pharmacia Biotech. The chromatographic ion exchange resin is chosen depending on the specific peptide to be purified and the conditions employed, such as pH, buffer, ionic strength etc., which are known to the person skilled in the art (that is, typically, pH below the isoelectric point (pI) of the peptide for cation exchange resins and pH above pI of the peptide for anion exchange resins, a sufficient buffer strength to maintain the desired pH, and a sufficiently low ionic strength possibly induced by the salt concentration), and includes but is not limited to Sepharose resins, Sephadex resins, Streamline resins, and Source resins from Amersham-Pharmacia Biotech, HyperD resins, Trisacryl resins, and Spherosil resins from BioSepra, TSK-gel resins and Toyopearl resins from TosoHaas, Fractogel EMD resins from Merck, Poros resins from Perseptive Biosystems, Macro-Prep resins from BioRAD, Expression resins from Whatman etc.

The term "a solution consisting essentially of an organic modifier, water, optionally a salt component and optionally a buffer" as used herein, is intended to mean a solution containing one or more organic modifiers, water, one or more salt components or no salt component and one or more buffers or no buffer, and optionally one or more further conventional components which the person skilled in the art would consider adding, according to conventional ion exchange chromatography processes.

The term "related impurities" as used herein, is intended to mean one or more impurities with a different local or overall net charge from the peptide, for instance truncated forms, all kinds of extended forms (extra amino acids, various derivatives including esters etc.), deamidated forms, incorrectly folded forms, forms with undesired glycosylation including sialylation, "lack of γ-carboxy glutamic acid", and others, as long as they elute before the peptide.

The term "pH-values", as used herein in connection with "at pH-values", "at the same or lower pH-values" and "at the same or higher pH-values", is intended to mean that the pH-value in step a) may be constant or may vary, typically, within 3 pH units, and subsequently, the pH-value in step b) may be at the same constant or varying pH-value as in step a), or may be at a different pH-value, which may be constant or may vary, typically, within 3 pH units. Such pH-values may typically be maintained or varied by addition of a buffer and/or an inorganic or organic acid or base, e.g. HCl, NaOH, $H_2O$, acetic acid, $NH_3$, KOH, $H_2SO_4$, citric acid.

The term "lower" as used herein, in connection with related impurities having a local or overall negative (or positive) net charge which is lower than the negative (or positive) net charge of the peptide, is intended to mean that the numeric value of the local or overall net charge of the related impurities is lower than the numeric value of the local or overall net charge of said peptide.

The present invention also relates to the following aspects:

Aspect 1. A cation exchange chromatography process for purifying a peptide from a mixture comprising said peptide and related impurities, comprising the steps of:

a) eluting said related impurities of said mixture in a solution consisting essentially of an organic modifier, water, optionally a salt component and optionally a buffer, at a linear or step gradient or isocratically in salt component, and at pH-values optionally maintained with a buffer so that said peptide has a positive local or overall net charge and said related impurities have a local or overall positive net charge which is lower than the positive net charge of said peptide so as to remove said related impurities, b) subsequently, eluting said peptide by a step or linear change to an aqueous solvent optionally with a salt component, at the same or higher pH-values optionally maintained with a buffer.

Aspect 2. An anion exchange chromatography process for purifying a peptide from a mixture comprising said peptide and related impurities, comprising the steps of:

a) eluting said related impurities of said mixture in a solution consisting essentially of an organic modifier, water, optionally a salt component and optionally a buffer, at a linear or step gradient or isocratically in salt component, and at pH-values optionally maintained with a buffer so that said peptide has a negative local or overall net charge and said related impurities have a local or overall negative net charge which is lower than the negative net charge of said peptide so as to remove said related impurities, b) subsequently, eluting said peptide by a step or linear change to an aqueous solvent optionally with a salt component, at the same or lower pH-values optionally maintained with a buffer.

Aspect 3. The process according to aspect 1 or 2 wherein the ratio of organic modifier to water on a weight percent basis is from 1:99 to 99:1.

Aspect 4. The process according to any one of aspects 1–3 wherein said organic modifier is selected from $C_{1-6}$-alkanol, $C_{1-6}$-alkenol or $C_{1-6}$-alkynol, urea, guanidine, or $C_{1-6}$-alkanoic acid, $C_{2-6}$-glycol, or $C_{3-7}$-polyalcohol including sugars.

Aspect 5. The process according to any one of aspects 14 wherein said salt component in step a) is selected from any organic or inorganic salt, preferably NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof.

Aspect 6. The process according to any one of aspects 14 wherein no salt component is present in step a.

Aspect 7. The process according to any one of aspects 1–5 wherein said salt component gradient in step a) is a step or linear salt component gradient.

Aspect 8. The process according to aspects 7 wherein said salt component is present in a concentration selected from the range of 0.1 mmol/kg to 3000 mmol/kg.

Aspect 9. The process according to any one of aspects 1–8 wherein said salt component in step b) is selected from any organic or inorganic salt, preferably NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof.

Aspect 10. The process according to any one of aspects 1–9 wherein in step b) said salt component is present in a concentration selected from the range of 0.1 mmol/kg to 3000 mmol/kg.

Aspect 11. The process according to any one of aspects 1–8 wherein no salt component is present in step b.

Aspect 12. The process according to any one of aspects 1–11 wherein said buffer in step a) or b) is independently selected from citrate buffers, phosphate buffers, tris buffers, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, tri-ethanol amine, imidazole buffers, pyridine buffers and barbiturate buffers and mixtures thereof.

Aspect 13. The process according to any one of aspects 1–12 wherein said buffer in step a) is present in a concentration selected from the range of 0.1 mmol/kg to 500 mmol/kg.

Aspect 14. The process according to any one of aspects 1–13 wherein said buffer in step b) is present in a concentration selected from the range of 0.1 mmol/kg to 1000 mmol/kg.

Aspect 15. The process according to any one of aspects 1–11 wherein no buffer is present in step a).

Aspect 16. The process according to any one of aspects 1–11 wherein no buffer is present in step b).

Aspect 17. A method for isolating a peptide, the method including purification of a peptide from a mixture containing said peptide and related impurities via a cation exchange chromatography process, the cation exchange chromatography process comprising the steps of:
  a) eluting said related impurities of said mixture in a solution consisting essentially of an organic modifier, water, optionally a salt component and optionally a buffer, at a linear or step salt component gradient or isocratically, and at pH-values optionally maintained with a buffer so that said peptide has a positive local or overall net charge and said related impurities have a local or overall positive net charge which is lower than the positive net charge of said peptide so as to remove said related impurities,
  b) subsequently, eluting said peptide by a step or linear change to an aqueous solvent optionally with a salt component, at the same or higher pH-values optionally maintained with a buffer;

and subsequently, if necessary, subjecting to analytical tests and/or further purification, and isolating said peptide in a conventional manner.

Aspect 18. A method for isolating a peptide, the method including purification of a peptide from a mixture containing said peptide and related impurities via an anion exchange chromatography process, the anion exchange chromatography process comprising the steps of:
  a) eluting said related impurities of said mixture in a solution consisting essentially of an organic modifier, water, optionally a salt component and optionally a buffer, at a linear or step salt component gradient or isocratically, and at pH-values optionally maintained with a buffer so that said peptide has a negative local or overall net charge and said related impurities have a local or overall negative net charge which is lower than the negative net charge of said peptide so as to remove said related impurities,
  b) subsequently, eluting said peptide by a step or linear change to an aqueous solvent optionally with a salt component, at the same or lower pH-values optionally maintained with a buffer;

and subsequently, if necessary, subjecting to analytical tests and/or further purification, and isolating said peptide in a conventional manner.

Aspect 19. The process or method according to any one of aspects 1–18 wherein said peptide to be purified is selected from polypeptides, oligopeptides, proteins, receptors, vira, as well as homologues, analogues and derivatives thereof, preferably glucagon, hGH, insulin, aprotinin, FVII, TPA, FVIIa, FFR-FVIIa, heparinase, ACTH, Heparin Binding Protein, corticotropin-releasing factor, angiotensin, calcitonin, insulin, glucagon-like peptide-1, glucagon-like peptide-2, insulin-like growth factor-1, insulin-like growth factor-2, fibroblast growth factors, gastric inhibitory peptide, growth hormone-releasing factor, pituitary adenylate cyclase activating peptides, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods, DPP IV, interleukins, immunoglobulins, complement inhibitors, serpin protease inhibitors, cytokines, cytokine receptors, PDGF, tumor necrosis factors, tumor necrosis factors receptors, growth factors, GIP, exendins, peptide histidine-methionine amide, helospectins, helodermin, pituitary adenylate cyclase activating peptide-related peptide, vasoactive intestinal polypeptide and analogues as well as derivatives thereof, more preferably glucagon, hGH, insulin, aprotinin, FVII, FVIIa, FFR-FVIIa, heparinase, glucagon-like peptide-1, glucagon-like peptide-2 and analogues as well as derivatives thereof, such as $Arg^{34}GLP-1(7-37)$, human insulin, and B28IsoAsp insulin.

EXAMPLES

The present invention is further illustrated by the following examples which, however, are not to be construed as limiting the scope of protection. The features disclosed in the foregoing description and in the following examples may, both separately and in any combination thereof, be material for realising the invention in diverse forms thereof.

Example 1

$Arg^{34}GLP-1(7-37)$ was expressed in yeast (*Sacch. cerevisiae*) by conventional recombinant DNA technology e.g as described in WO 98/08871. $Arg^{34}GLP-1(7-37)$ fermentation broth was purified by a conventional reverse phase chromatography capture step, and subsequently precipitated at the pI (isoelectric point) of $Arg^{34}GLP-1(7-37)$. 2 g of the precipitate containing $Arg^{34}GLP-1(7-37)$ and the truncated form missing a histidine and an alanine residue, $Arg^{34}GLP-1(9-37)$, as one of several impurities was suspended in 100 ml water and dissolved by pH adjustment to 8.2. The resulting mixture was adjusted to pH 3.4 and filtered. 21 ml of the filtrate was applied to a 20 ml Source 30S (Amersham Pharmacia Biotech) column equilibrated with 100 ml 20 mmol/kg citric acid, 75 mmol/kg KCl, 45% w/w ethanol, pH 3.5. The truncated form was eluted/washed off by a step gradient of 60 ml 20 mmol/kg citric acid, 87.5 mmol/kg KCl, 45% w/w ethanol, pH 3.5. The target peptide, $Arg^{34}GLP-1(7-37)$, was eluted in a single peak by a step gradient of 100 ml 200 mmol/kg Tris-hydroxymethyl amino-methane, pH 8.5. A chromatogram is shown in FIG. 1.

RP-HPLC analysis for identification/verification of collected peaks was carried out on a $C_{18}$-substituted 120 Å silica (YMC) 4.0×250 mm column with 5 μm particles. Buffer A consisted of 0.15 M $(NH_4)_2SO_4$ in 7.8% acetonitrile, pH 2.5, and buffer B contained 63.4% acetonitrile. Linear gradients from 37–41% B in 12 min followed by 41–100% B in 15 min were run at a flow rate of 1 ml/min. The chromatographic temperature was kept at 60° C. and UV detection was performed at 214 nm. Analytical results were:

|  | $Arg^{34}GLP-1-$ (7-37)content | $Arg^{34}GLP-1-$ (9-37)content |
| --- | --- | --- |
| Sample for application | 48% | 18% |
| Wash containing ethanol | 1% | 76% |
| Aqueous eluate | 65% | 1% |

Figure 2:
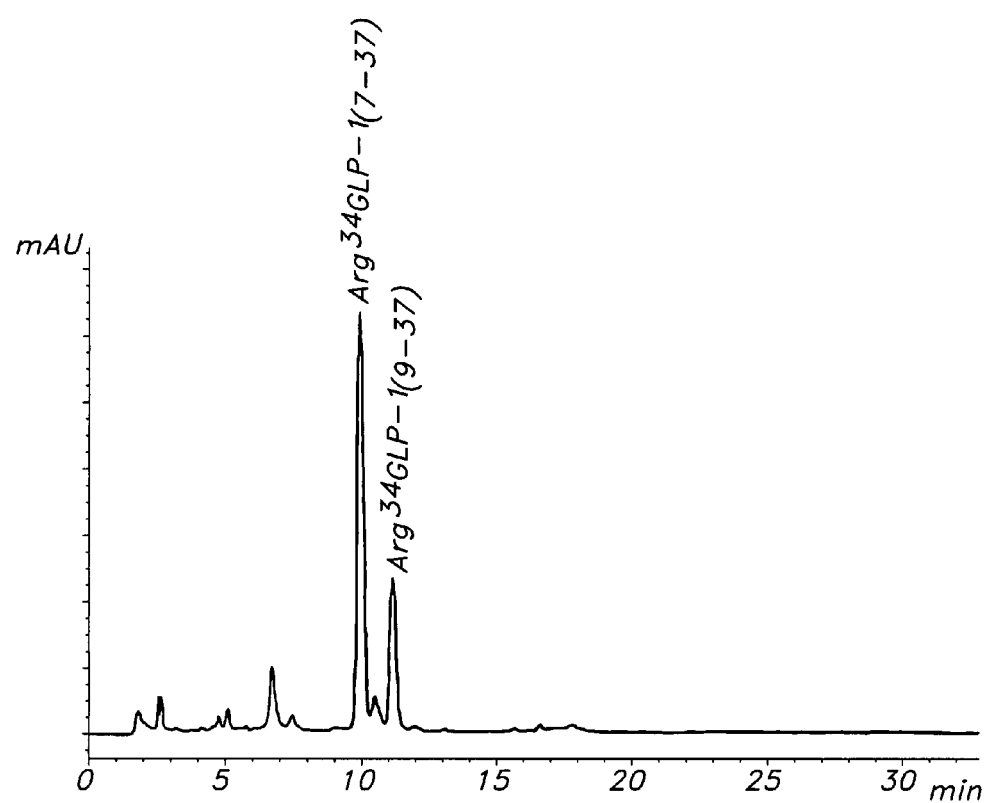
FIGS. 2–3 are chromatographs of the sample for application and the eluate obtained as described in Example 1.
Figure 3:
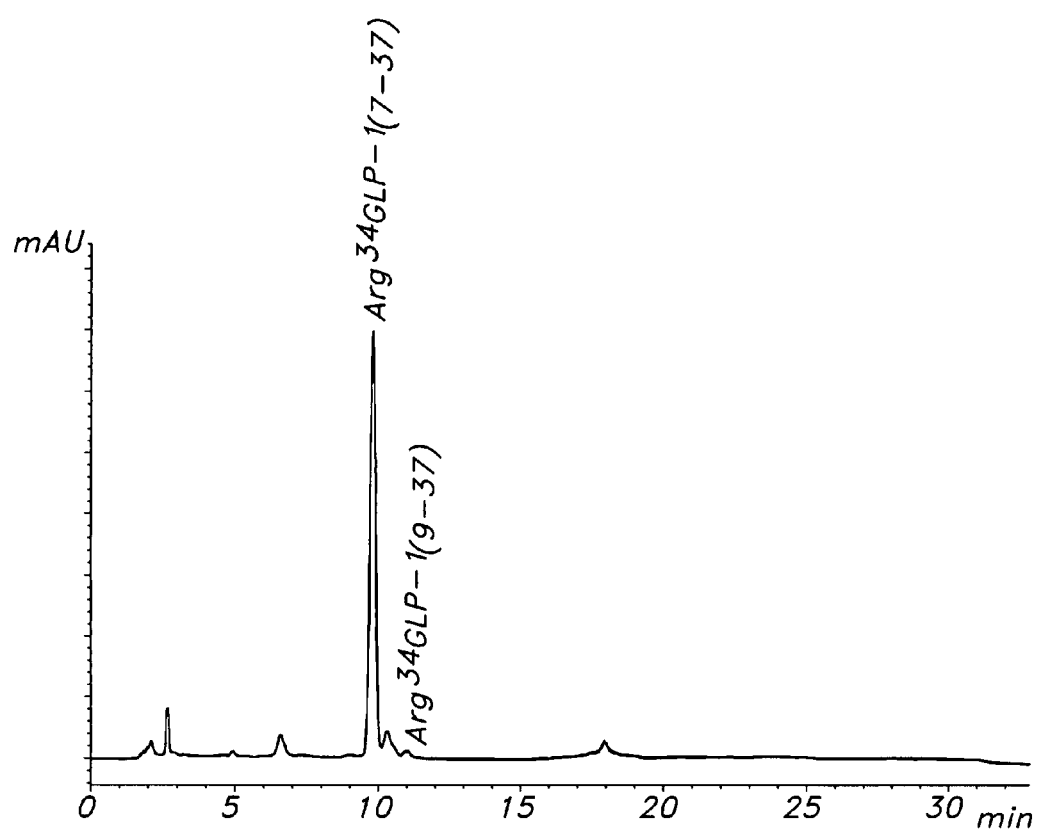

Chromatograms of the sample for application and the eluate is shown in FIGS. 2 and 3, respectively. The analytical results show a selective removal of the truncated form by the wash step containing ethanol and a high reduction of the truncated form in the aqueous eluate by employment of the cation exchange chromatography method.

Example 2

Arg$^{34}$GLP-1(7-37) fermentation broth was purified by cation exchange chromatography and precipitated as described in Example 1.

2 g of the precipitate containing Arg$^{34}$GLP-1 (7-37) and the truncated form, Arg$^{34}$GLP-1 (9-37), as one impurity was suspended and dissolved in 100 ml 20 mmol/kg glycin, pH 9.0 resulting in a final pH of 8.4. The resulting mixture was adjusted to pH 3.5 and filtered. 52 ml of the filtrate was applied to a 20 ml Source 30S (Amersham Pharmacia Biotech) column equilibrated with 60 ml 20 mmol/kg citric acid, 75 mmol/kg KCl, 45% w/w ethanol, pH 3.5. The truncated form was eluted/washed off by a step gradient of 60 ml 20 mmol/kg citric acid, 87.5 mmol/kg KCl, 45% w/w ethanol, pH 3.5. The target peptide, Arg$^{34}$GLP-1(7-37), was eluted in a single peak by a step gradient of 100 ml 200 mmol/kg glycin, pH 9.0. RP-HPLC analysis for identification/verification of collected peaks was carried out as described in Example 1. The analytical results show a selective removal of the truncated form by the wash step containing ethanol and a high reduction of the truncated form in the aqueous eluate by employment of the cation exchange chromatography method.

Example 3

Figure 4:
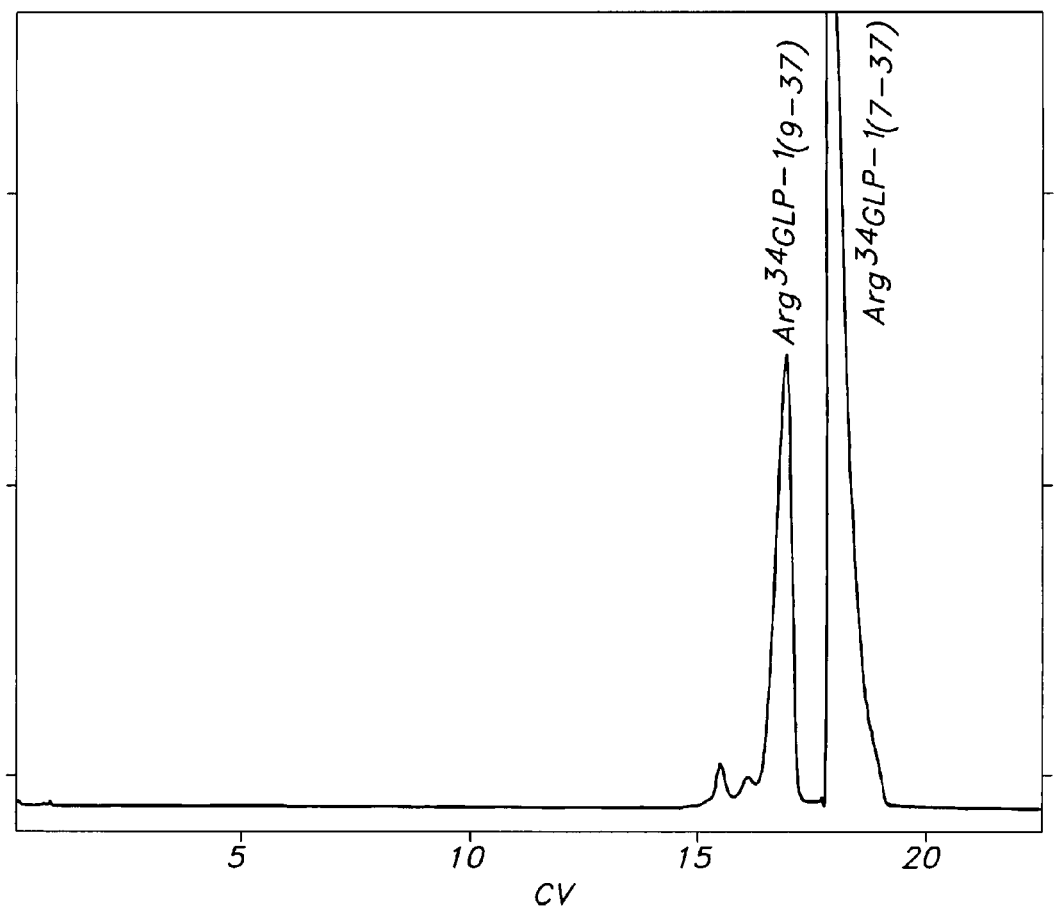
FIG. 4 is a chromatograph obtained as described in Example 3.

Arg$^{34}$GLP-1(7-37) fermentation broth was purified by a conventional cation exchange chromatography capture step followed by a conventional RP-HPLC purification step. 4 volumes of water was added to the RP-HPLC pool containing Arg$^{34}$GLP-1 (7-37) and the truncated form, Arg$^{34}$GLP-1(9-37), as an impurity. 175 ml of the resulting solution was adjusted to pH 3.5 and applied to a 20 ml Source 30S (Amersham Pharmacia Biotech) column equilibrated with 100 ml 20 mmol/kg citric acid, 75 mmol/kg KCl, 45% w/w ethanol, pH 3.5. The column was washed with 20 ml equilibration solution, and the truncated form was eluted/washed off by a linear gradient from 75 to 100 mmol/kg KCl (20 mmol/kg citric acid, 45% w/w ethanol, pH 3.5). The target peptide, Arg$^{34}$GLP-1(7-37), was eluted in a single peak by a step gradient of 100 ml 100 mmol/kg Na$_2$CO$_3$, pH 9.5. A chromatogram is shown in FIG. 4.

Example 4

Arg$^{34}$GLP-1 (7-37) was expressed, captured by cation exchange, and purified by RP-HPLC as described in Example 3.

1 volume of water was added to the RP-HPLC pool containing Arg$^{34}$GLP-1(7-37) and the truncated form, Arg$^{34}$GLP-1(9-37), as an impurity. 86 ml of the resulting solution was adjusted to pH 3.5 and applied to a 20 ml Source 30S (Amersham Pharmacia Biotech) column equilibrated with 100 ml 20 mmol/kg citric acid, 75 mmol/kg KCl, 45% w/w ethanol, pH 3.5. The column was washed with 20 ml equilibration solution, and the truncated form was eluted/washed off by a linear gradient from 75 to 100 mmol/kg KCl (20 mmol/kg citric acid, 45% w/w ethanol, pH 3.5). The target peptide, Arg$^{34}$GLP-1(7-37), was eluted by a step gradient of 100 ml 100 mmol/kg H$_3$BO$_3$, 100 mmol/kg NaCl, pH 9.5.

Example 5

Arg$^{34}$GLP-1 (7-37) was isolated from the fermentation broth by conventional reverse phase chromatography and precipitated as described in Example 1.

Figure 5:
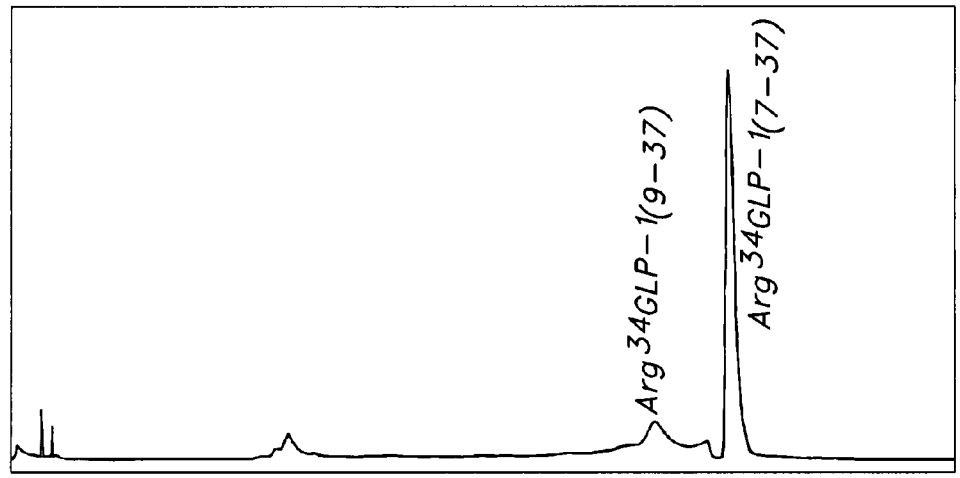
FIG. 5 is a chromatograph obtained as described in Example 5.

10 g of the precipitate containing Arg$^{34}$GLP-1(7-37) and the truncated form, Arg$^{34}$GLP-1(9-37), as one of several impurities was suspended in 500 ml water and dissolved by pH adjustment to 8.3 to a Arg$^{34}$GLP-1(7-37) concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 34% w/w ethanol, pH 3.5. The truncated form was eluted/washed off by a linear gradient from 0 to 1.29% w/w KCl (0.42% w/w citric acid, 34% w/w ethanol, pH 3.5). The target peptide, Arg$^{34}$GLP-1(7-37), was eluted in a single peak by a step gradient of 100 ml 200 mmol/kg glycin, pH 9.5. A chromatogram is shown in FIG. 5.

Example 6

Arg$^{34}$GLP-1 (7-37) was isolated from the fermentation broth by conventional reverse phase chromatography and precipitated as described in Example 1.

10 g of the precipitate containing Arg$^{34}$GLP-1(7-37) and the truncated form, Arg$^{34}$GLP-1(9-37), as one of several impurities was suspended in 500 ml water and dissolved by pH adjustment to 8.3 to a Arg$^{34}$GLP-1 (7-37) concentration of approximately 1.6 mg/ml. 5 ml of the resulting solution was adjusted to pH 3.2 and applied to a 20 ml Source 30S (Amersham Pharmacia Biotech) column equilibrated with 60 ml 0.42% w/w citric acid, 29% w/w ethanol, pH 3.5. The truncated form was eluted/washed off by a linear gradient from 0 to 1.96% w/w KCl (0.42% w/w citric acid, 29% w/w ethanol, pH 3.5). The target peptide, Arg$^{34}$GLP-1(7-37), was eluted by a step gradient of 100 ml 200 mmol/kg glycin, pH 9.5.

Example 7

Arg$^{34}$GLP-1 (7-37) was isolated from the fermentation broth by conventional reverse phase chromatography and precipitated as described in Example 1.

10 g of the precipitate containing Arg$^{34}$GLP-1(7-37) and the truncated form, Arg$^{34}$GLP-1 (9-37), as one of several impurities was suspended in 500 ml water and dissolved by pH adjustment to 8.3 to a Arg$^{34}$GLP-1 (7-37) concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 51% w/w ethanol, pH 3.5. The truncated form was eluted/washed off by a linear gradient from 0 to 1.00% w/w KCl (0.42% w/w citric acid, 51% w/w ethanol, pH 3.5). The target peptide, Arg$^{34}$GLP-1(7-37), was eluted by a step gradient of 100 ml 200 mmol/kg glycin, pH 9.5.

Example 8

Arg$^{34}$GLP-1 (7-37) was isolated from the fermentation broth by conventional reverse phase chromatography and precipitated as described in Example 1.

10 g of the precipitate containing Arg$^{34}$GLP-1 (7-37) and the truncated form, Arg$^{34}$GLP-1(9-37), as one of several impurities was suspended in 500 ml water and dissolved by pH adjustment to 8.3 to a Arg$^{34}$GLP-1(7-37) concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 71% w/w ethanol, pH 3.5. The truncated form was eluted/washed off by a linear gradient from 0 to 0.48% w/w KCl (0.42% w/w citric acid, 71% w/w ethanol, pH 3.5). The target peptide, Arg$^{34}$GLP-1(7-37), was eluted by a step gradient of 100 ml 200 mmol/kg glycin, pH 9.5.

Example 9

Arg$^{34}$GLP-1(7-37) was isolated from the fermentation broth by conventional reverse phase chromatography and precipitated as described in Example 1.

Figure 6:
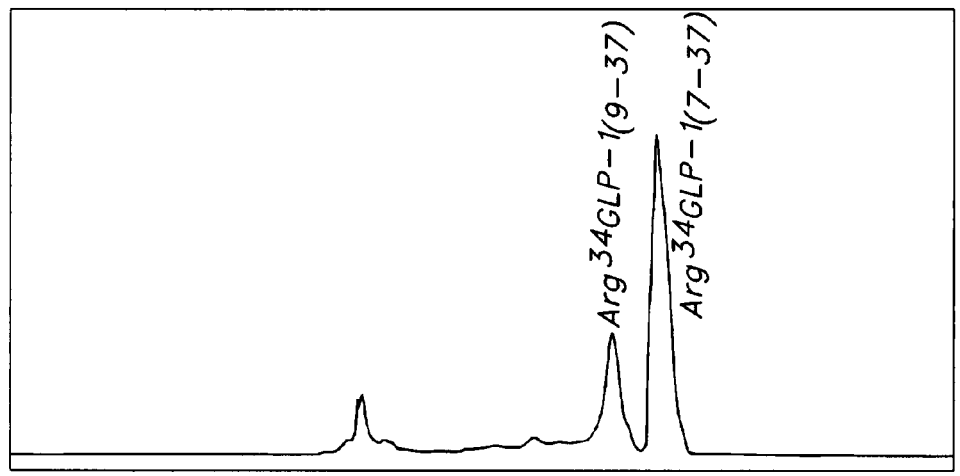
FIG. 6 is a chromatograph obtained as described in Example 9.

10 g of the precipitate containing Arg$^{34}$GLP-1(7-37) and the truncated form, Arg$^{34}$GLP-1(9-37), as one of several impurities was suspended in 500 ml water and dissolved by pH adjustment to 8.3 to a Arg$^{34}$GLP-1 (7-37) concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 40% w/w 2-propanol, pH 3.5. The truncated form was eluted/washed off by a linear gradient from 0 to 0.61% w/w KCl (0.42% w/w citric acid, 40% w/w 2-propanol, pH 3.5). The target peptide, Arg$^{34}$GLP-1(7-37), was eluted in a single peak by a step gradient of 100 ml 200 mmol/kg glycin, pH 9.5. A chromatogram is shown in FIG. 6.

Example 10

Arg$^{34}$GLP-1 (7-37) was isolated from the fermentation broth by conventional reverse phase chromatography and precipitated as described in Example 1.

Figure 7:
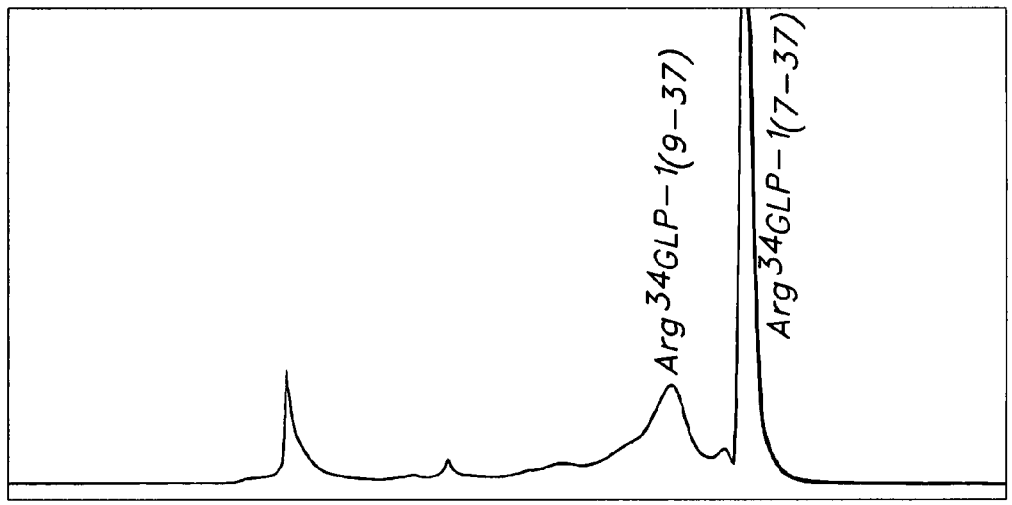
FIG. 7 is a chromatograph obtained as described in Example 10.

10 g of the precipitate containing Arg$^{34}$GLP-1(7-37) and the truncated form, Arg$^{34}$GLP-1(9-37), as one of several impurities was suspended in 500 ml water and dissolved by pH adjustment to 8.3 to a Arg$^{34}$GLP-1 (7-37) concentration of approximately 1.6 mg/ml. 5 ml of the resulting solution was adjusted to pH 3.5 and applied to a 8 ml Poros 50 HS (PE Biosystems) column equilibrated with 24 ml 0.42% w/w citric acid, 51% w/w ethanol, pH 3.5. The truncated form was eluted/washed off by a linear gradient from 0 to 1.34% w/w KCl (0.42% w/w citric acid, 51% w/w ethanol, pH 3.5). The target peptide, Arg$^{34}$GLP-1(7-37), was eluted by a step gradient of 40 ml 200 mmol/kg glycin, pH 9.5. A chromatogram is shown in FIG. 7.

Example 11

Arg$^{34}$GLP-1 (7-37) was isolated from the fermentation broth by conventional reverse phase chromatography and precipitated as described in Example 1.

Figure 8:
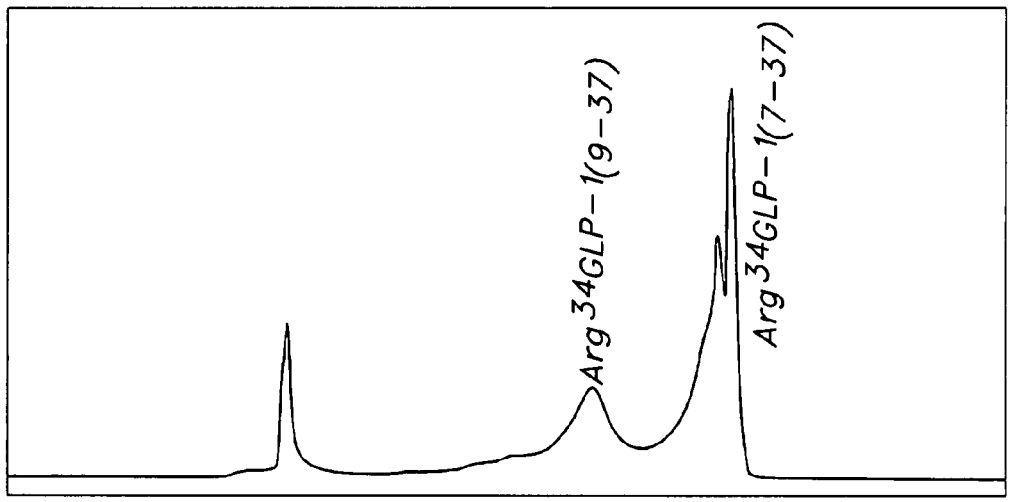
FIG. 8 is a chromatograph obtained as described in Example 11.

10 g of the precipitate containing Arg$^{34}$GLP-1(7-37) and the truncated form, Arg$^{34}$GLP-1(9-37), as one of several impurities was suspended in 500 ml water and dissolved by pH adjustment to 8.3 to a Arg$^{34}$GLP-1(7-37) concentration of approximately 1.6 mg/ml. 5 ml of the resulting solution was adjusted to pH 3.5 and applied to a 8 ml Poros 50 HS (PE Biosystems) column equilibrated with 24 ml 0.42% w/w citric acid, 40% w/w 2-propanol, pH 3.5. The truncated form was eluted/washed off by a linear gradient from 0 to 1.34% w/w KCl (0.42% w/w citric acid, 40% w/w 2-propanol, pH 3.5). The target peptide, Arg$^{34}$GLP-1 (7-37), was eluted by a step gradient of 40 ml 200 mmol/kg glycin, pH 9.5. A chromatogram is shown in FIG. 8.

Example 12

Arg$^{34}$GLP-1 (7-37) was isolated from the fermentation broth by conventional reverse phase chromatography and precipitated as described in Example 1.

Figure 9:
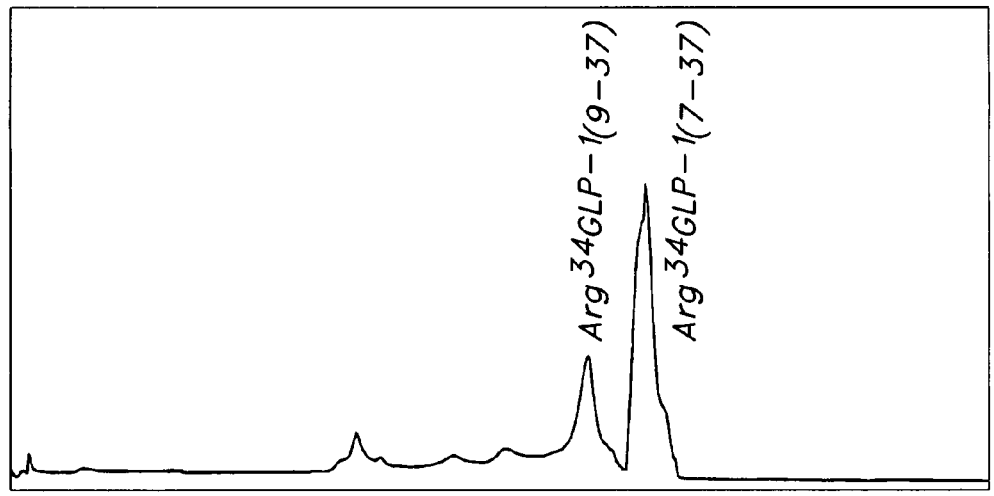
FIG. 9 is a chromatograph obtained as described in Example 12.

10 g of the precipitate containing Arg$^{34}$GLP-1(7-37) and the truncated form, Arg$^{34}$GLP-1(9-37), as one of several impurities was suspended in 500 ml water and dissolved by pH adjustment to 8.3 to a Arg$^{34}$GLP-1 (7-37) concentration of approximately 1.6 mg/ml. 5 ml of the resulting solution was adjusted to pH 3.5 and applied to a 20 ml Source 30S (Amersham Pharmacia Biotech) column equilibrated with 60 ml 0.42% w/w citric acid, 40% w/w 2-methyl-2,4-pentanediol, pH 3.5. The truncated form was eluted/washed off by a linear gradient from 0 to 0.60% w/w KCl (0.42% w/w citric acid, 40% w/w 2-methyl-2,4-pentanediol, pH 3.5). The target peptide, Arg$^{34}$GLP-1(7-37), was eluted in a single peak by a step gradient of 100 ml 200 mmol/kg glycin, pH 9.5. A chromatogram is shown in FIG. 9.

Example 13

Figure 10:
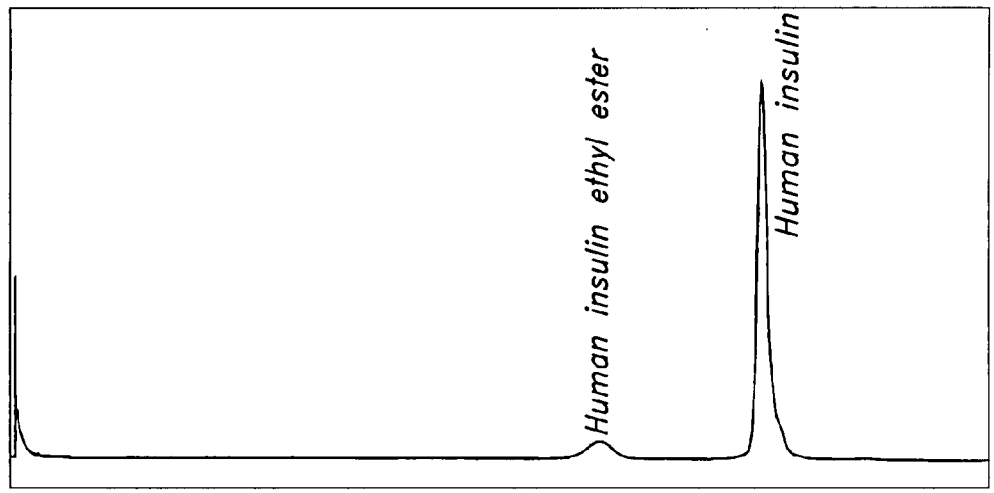
FIG. 10 is a chromatograph obtained as described in Example 13.

A mixture of 7.7 mg/ml human insulin and 0.8 mg/ml human insulin ethyl ester (B30) was obtained by conventional methods as described elsewhere (cf. I. Mollerup, S. W. Jensen, P. Larsen, O. Schou, L. Snel: Insulin, Purification, in M. C. Flickinger, S. W. Drew: Encyclopedia of Bioprocess Technology: Fermentation, Biocatalysis, and Bioseparation, John Wiley & Sons, 1999). The mixture contained 4 mmol/l EDTA, 16% w/w ethanol, pH 7.5. 2 ml of the mixture was applied to a 20 ml TSK-Gel Q-5PW (TosoHaas) column equilibrated with 40 ml 0.15% w/w triethanolamine, 42.5% w/w ethanol, pH 7.5. The human insulin ethyl ester impurity was eluted/washed off by a linear gradient from 0 to 1.14% w/w sodium citrate tri-hydrate (0.15% w/w triethanolamine, 42.5% w/w ethanol, pH 7.5). The target protein, human insulin, was eluted in a single peak by a step gradient of 60 ml 2.72% w/w sodium citrate tri-hydrate, 0.15% w/w triethanolamine, pH 7.5. A chromatogram is shown in FIG. 10.

Example 14

Figure 11:
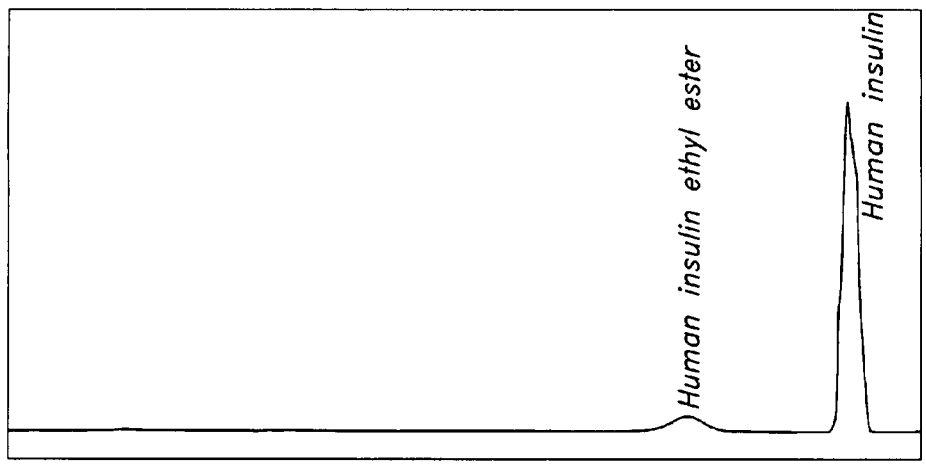
FIG. 11 is a chromatograph obtained as described in Example 14.

A mixture of human insulin and human insulin ethyl ester (B30) was obtained as described in Example 13. 2 ml of the mixture was applied to a 20 ml TSK-Gel Q-5PW (TosoHaas) column equilibrated with 40 ml 0.15% w/w triethanolamine, 42.5% w/w ethanol, pH 7.5. The human insulin ethyl ester impurity was eluted/washed off by a linear gradient from 0 to 0.90% w/w sodium citrate tri-hydrate (0.15% w/w triethanolamine, 42.5% w/w ethanol, pH 7.5). The target protein, human insulin, was eluted in a single peak by a step gradient of 60 ml 100 mmol/l citric acid, pH 3. A chromatogram is shown in FIG. 11.

Example 15

A mixture of human insulin and human insulin ethyl ester (B30) was obtained as described in Example 13. 2 ml of the mixture was applied to a 20 ml TSK-Gel Q-5PW (TosoHaas) column equilibrated with 40 ml 0.15% w/w triethanolamine, 71% w/w ethanol, pH 7.5. The human insulin ethyl ester impurity was eluted/washed off by a linear gradient from 0 to 1.63% w/w sodium citrate tri-hydrate (0.15% w/w triethanolamine, 71% w/w ethanol, pH 7.5). The target protein, human insulin, was eluted in a single peak by a step gradient of 60 ml 2.72% w/w sodium citrate tri-hydrate, 0.15% w/w triethanolamine, pH 7.5.

Example 16

Figure 12:
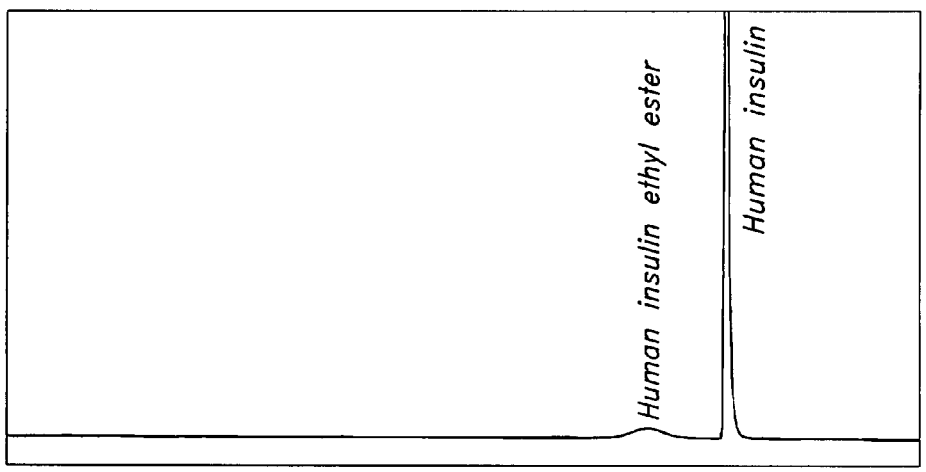
FIG. 12 is a chromatograph obtained as described in Example 16.

A mixture of 9.0 mg/ml human insulin and 0.6 mg/ml human insulin ethyl ester (B30) was obtained as described in Example 13. The mixture contained 4 mmol/l EDTA, pH 7.5 with a human insulin concentration of 9 mg/ml. 2 ml of the mixture was applied to a 20 ml TSK-Gel Q-5PW (TosoHaas) column equilibrated with 40 ml 0.15% w/w triethanolamine, 81% w/w ethanol, pH 7.5. The human insulin ethyl ester impurity was eluted/washed off by a linear gradient from 0 to 2.18% w/w sodium citrate tri-hydrate (0.15% w/w triethanolamine, 81% w/w ethanol, pH 7.5). The target protein, human insulin, was eluted in a single peak by a step gradient of 60 ml 2.72% w/w sodium citrate tri-hydrate, 0.15% w/w triethanolamine, pH 7.5. A chromatogram is shown in FIG. 12.

Example 17

A mixture of human insulin and human insulin ethyl ester (B30) was obtained as described in Example 16. 2 ml of the mixture was applied to a 20 ml TSK-Gel Q-5PW (TosoHaas) column equilibrated with 40 ml 0.15% w/w triethanolamine, 51% w/w ethanol, pH 7.5. The human insulin ethyl ester impurity was eluted/washed off by a linear gradient from 0 to 1.09% w/w sodium citrate tri-hydrate (0.15% w/w triethanolamine, 51% w/w ethanol, pH 7.5). The target protein, human insulin, was eluted in a single peak by a step gradient of 60 ml 2.72% w/w sodium citrate tri-hydrate, 0.15% w/w triethanolamine, pH 7.5.

What is claimed is:

1. A method for purifying a peptide from a mixture comprising said peptide and related impurities, said method comprising:
    a) eluting said related impurities of said mixture from an anion exchange chromatography matrix using a solution comprising an organic modifier, water, a buffer, and optionally a salt component at a linear or step gradient or isocratically in salt component, and at pH-values maintained with a buffer so that said peptide has a negative local or overall net charge and said related impurities have a local or overall negative net charge which is lower than the negative net charge of said peptide so as to remove said related impurities; and without an intervening step,
    b) subsequently, eluting said peptide in the absence of an organic modifier, by a step or linear change to an aqueous solvent optionally with a salt component, at the same or lower pH-values maintained with a buffer.

2. The method according to claim 1 further comprising subjecting the peptide eluted in step (b) to analytical tests and/or further purification.

3. The method of claim 1, wherein said peptide to be purified is selected from polypeptides, oligopeptides, proteins, and receptors.

4. The method of claim 1, wherein said peptide to be purified is selected from glucagon, hGH, insulin, FactorVII, FactorVIIa, FactorVIIai, FFR-FactorVIIa, glucagon-like peptide-1, glucagon-like peptide-2 and analogs thereof.

5. The method of claim 1, wherein the ratio of organic modifier to water on a weight percent basis is from 1:99 to 99:1.

6. The method of claim 1, wherein the organic modifier is selected from $C_{1-6}$alkanol, $C_{1-6}$alkenol, $C_{1-6}$-alkynol, urea, guanidine, $C_{1-6}$-alkanoic acid, $C_{2-6}$-glycol, or $C_{3-7}$-polyalcohol.

7. The method according to claim 1, wherein the peptide is selected from the group consisting of $Val^8GLP$-1(7-37), $Thr^8GLP$-1(7-37), $Met^8GLP$-1(7-37), $Gly^8GLP$-1(7-37), $Val^8GLP$-1(7-36) amide, $Thr^8GLP$-1(7-36) amide, $Met^8GLP$-1(7-36) amide, $Gly^8GLP$-1(7-36) amide, $Arg^{34}GLP$-1(7-37), and B28IsoAsp insulin.

8. An industrial method for producing a pure peptide from a mixture comprising said peptide and related impurities, said method comprising:
    a) eluting said related impurities of said mixture from an anion exchange chromatography matrix using a solution comprising an organic modifier, water, a buffer, and optionally a salt component at a linear or step gradient or isocratically in salt component, and at pH-values maintained with a buffer so that said peptide has a negative local or overall net charge and said related impurities have a local or overall negative net charge which is lower than the negative net charge of said peptide so as to remove said related impurities; and without an intervening step,
    b) subsequently, eluting said peptide in the absence of an organic modifier, by a step or linear change to an aqueous solvent optionally with a salt component, at the same or lower pH-values maintained with a buffer.

9. The method according to claim 8 further comprising subjecting the peptide eluted in step (b) to analytical tests and/or further purification.

10. The method according to claim 8, wherein said peptide to be purified is selected from polypeptides, oligopeptides, proteins, and receptors.

11. The method according to claim 8, wherein said peptide to be purified is selected from glucagon, hGH, insulin, FactorVII, FactorVIIa, FactorVIIai, FFR-FactorVIIa, glucagon-like peptide-1, glucagon-like peptide-2 and analogs thereof.

12. The method according to claim 8, wherein the ratio of organic modifier to water on a weight percent basis is from 1:99 to 99:1.

13. The method according to claim 8, wherein the organic modifier is selected from $C_{1-6}$alkanol, $C_{1-6}$alkenol, $C_{1-6}$alkynol, urea, guanidine, $C_{1-6}$-alkanoic acid, $C_{2-6}$-glycol, or $C_{3-7}$-polyalcohol.

14. A method for purifying a peptide selected from glucagon, hGH, insulin, FactorVII, FactorVIIa, FactorVIIai, FFR-FactorVIIa, glucagon-like peptide-1, and glucagon-like peptide-2 and analogs thereof from a mixture comprising said peptide and related impurities, said method comprising:
    a) eluting said related impurities of said mixture from an anion exchange chromatography matrix using a solution comprising an organic modifier, water, a buffer, and optionally a salt component at a linear or step gradient or isocratically in salt component, and at pH-values maintained with a buffer so that said peptide has a negative local or overall net charge and said related impurities have a local or overall negative net charge which is lower than the negative net charge of said peptide so as to remove said related impurities; and
    b) subsequently, eluting said peptide in the absence of an organic modifier, by a step or linear change to an aqueous solvent optionally with a salt component, at the same or lower pH-values maintained with a buffer.

15. The method according to claim 14, wherein said peptide is glucagon-like peptide-1 or an analog thereof.

16. The method according to claim 15, wherein said glucagon-like peptide-1 analog is selected from the group consisting of $Val^8GLP-1(7-37)$, $Thr^8GLP-1(7-37)$, $Met^8GLP-1(7-37)$, $Gly^8GLP-1(7-37)$, $Val^8GLP-1(7-36)$ amide, $Thr^8GLP-1(7-36)$ amide, $Met^8GLP-1(7-36)$ amide, $Gly^8GLP-1(7-36)$ amide and $Arg^{34}GLP-1(7-37)$.

17. The method according to claim 14, wherein said peptide is insulin or an analog thereof.

18. The method according to claim 17, wherein said insulin analog is B28IsoAsp insulin.

19. The method according to claim 14, wherein the solution used to elute related impurities from the anion exchange chromatography matrix in step (a) includes a salt component.

20. The method according to claim 19, wherein the related impurities are eluted from the anion exchange chromatography matrix in step (a) with a linear gradient in the salt component.

21. The method according to claim 19, wherein the organic modifier in the solution used to elute related impurities from the anion exchange chromatography matrix in step (a) is a $C_1$–$C_6$ alkanol.

* * * * *